(12) United States Patent
Lan et al.

(10) Patent No.: US 11,473,765 B1
(45) Date of Patent: Oct. 18, 2022

(54) ELECTRIC LIGHT SOURCE DEVICE AND LAMP

(71) Applicant: Shenzhen Guanke Technologies Co., Ltd, Shenzhen (CN)

(72) Inventors: Qing Lan, Shenzhen (CN); Shoubao Chen, Shenzhen (CN); Ligen Liu, Shenzhen (CN); Xuren Qiu, Shenzhen (CN)

(73) Assignee: Shenzhen Guanke Technologies Co., Ltd, Shenzhen (CN)

( * ) Notice: Subject to any disclaimer, the term of this patent is extended or adjusted under 35 U.S.C. 154(b) by 0 days.

(21) Appl. No.: 17/411,459

(22) Filed: Aug. 25, 2021

(30) Foreign Application Priority Data

Jun. 23, 2021 (CN) .......................... 202121411135.9

(51) Int. Cl.
| | | |
|---|---|---|
| *F21V 23/04* | (2006.01) | |
| *F21V 7/04* | (2006.01) | |
| *F21V 7/24* | (2018.01) | |
| *F21V 15/02* | (2006.01) | |
| *G01N 22/00* | (2006.01) | |

(Continued)

(52) U.S. Cl.
CPC .......... *F21V 23/0471* (2013.01); *F21V 7/005* (2013.01); *F21V 7/043* (2013.01); *F21V 7/24* (2018.02); *F21V 15/02* (2013.01); *G01N 22/00* (2013.01); *A61L 2/10* (2013.01); *A61L 9/20* (2013.01); *A61L 2202/11* (2013.01);
(Continued)

(58) Field of Classification Search
CPC .......... A61L 9/20; A61L 2/10; A61L 2202/11; A61L 2209/12; F21V 17/16; F21V 17/162; F21V 15/02; F21V 7/005; F21V 17/164; F21V 23/0471; F21Y 2103/37; F21Y 2111/00; H01J 61/327
See application file for complete search history.

(56) References Cited

U.S. PATENT DOCUMENTS

| | | | |
|---|---|---|---|
| 5,577,835 A * | 11/1996 | Huang .................... | H05B 41/00 362/650 |
| 6,400,104 B1 * | 6/2002 | Ham ...................... | H01J 61/96 315/56 |

(Continued)

FOREIGN PATENT DOCUMENTS

| | | | | | |
|---|---|---|---|---|---|
| CN | 107781663 A | * | 3/2018 | ............. | F21K 9/232 |
| CN | 208397921 U | * | 1/2019 | ................ | F21S 9/00 |

(Continued)

*Primary Examiner* — Colin J Cattanach
(74) *Attorney, Agent, or Firm* — Maier & Maier, PLLC

(57) ABSTRACT

Disinfection equipment, particularly an electric light source device and lamp. The electric light source device includes a lamp cap, a lamp housing, a connecting fitting, a reflection column and a supporting fitting which are connected in sequence from the top to the bottom and the electric light source device also includes a lamp tube, a net enclosure and a driving power supply provided inside the lamp housing, where the lamp tube includes several tubes which are connected in sequence and are provided around the reflection column, the end of the first tube and that of the last tube are respectively provided with the first electrode and the second electrode which respectively electrically connect to the driving power supply, the lamp housing is provided at one end of the tube with an electrode, and the lamp tube can emit 360° light around the reflection column.

7 Claims, 9 Drawing Sheets

(51) Int. Cl.
*F21V 7/00* (2006.01)
*F21Y 103/37* (2016.01)
*F21Y 107/00* (2016.01)
*A61L 9/20* (2006.01)
*A61L 2/10* (2006.01)

(52) U.S. Cl.
CPC ....... *A61L 2209/12* (2013.01); *F21Y 2103/37* (2016.08); *F21Y 2107/00* (2016.08)

(56) References Cited

U.S. PATENT DOCUMENTS

| | | | |
|---|---|---|---|
| 11,226,088 B2* | 1/2022 | Lan | F21V 15/00 |
| 2002/0057059 A1* | 5/2002 | Ogishi | H01J 61/28 |
| | | | 313/636 |
| 2006/0114670 A1* | 6/2006 | Ho | H01J 61/327 |
| | | | 362/225 |
| 2019/0037657 A1* | 1/2019 | Lan | F21V 17/002 |
| 2019/0162371 A1* | 5/2019 | Lan | F21V 23/02 |
| 2021/0393822 A1* | 12/2021 | Chen | B60S 3/008 |

FOREIGN PATENT DOCUMENTS

| | | | | |
|---|---|---|---|---|
| CN | 110671617 A | * | 1/2020 | ......... F16C 29/0616 |
| CN | 110715274 A | * | 1/2020 | ............. F21V 15/02 |
| CN | 111135322 A | * | 5/2020 | |
| CN | 111293414 A | * | 6/2020 | |

* cited by examiner

ELECTRIC LIGHT SOURCE DEVICE AND LAMP

TECHNICAL FIELD

The present invention relates to the technical field of lighting and sterilization equipment, particularly to an electric light source device and lamp.

BACKGROUND

The electric light source device is mainly provided inside the lamp enclosure or on the lamp base for use. The light source of existing UV electric light source device mainly adopts two kinds of light sources: UV LED lamp bead and UV lamp tube, wherein the UV lamp tube refers to gas discharge UV lamp tube light sources like low-pressure mercury lamp, high and medium-pressure mercury lamp, xenon lamp, etc. Compared with the UV light LED lamp bead, the UV lamp tube is characterized by high UV light conversion efficiency and low cost, so it is more suitable for large-power UV electric light source device.

Usually, UV sterilization electric light source device with power greater than 40 W usually needs to adopt several UV lamp tubes to improve its power and shorten its UV sterilization time. Such products mainly have the following problems:

(1) Several UV lamp tubes and several driving power supply devices are needed, each UV lamp tube needs to connect four power supply output ends, so electrical connection is difficult, and the cost of lamp tubes and driving power supply is high.

(2) The product has a large volume, it is hard to directly install the product inside the ordinary lamp enclosure for use, the compatibility is poor, and it is inconvenient in use.

(3) The product does not have a protective structure or has a complex protective structure.

The foregoing content is only used for assisting in understanding the technical scheme of this utility model, but does not mean the acknowledgement of that the above content is the current technology.

SUMMARY

To solve many technical problems of large-power UV germicidal lights as mentioned above, the main objective of the present invention is to provide an electric light source device and lamp.

To realize the above subjective of the utility model, this invention adopts the following technical solution:

An electric light source device, characterized in that: the electric light source device comprises a lamp cap, a lamp housing, a connecting fitting, a reflection column and a supporting fitting which are connected in sequence from the top to the bottom and also a lamp tube, a net enclosure and the driving power supply provided inside the lamp housing;

the lamp tube provided at the bottom of the connecting fitting comprises several tubes which are connected in sequence and are provided around the reflection column, the end of the first the tube and that of the last tube are provided with the first electrode and the second electrode respectively, and the first electrode and the second electrode electrically connect to the driving power supply respectively;

the net enclosure is provided on the outer side of the lamp tube and connects to the connecting fitting or the lamp housing, and the net enclosure is provided with several first light outlets along which UV light emitted by the lamp tube can go out of the product.

Other characteristics and corresponding beneficial effects of the present invention are elaborated in the latter part of the description.

The solving ideas of technical problems of the present invention and relevant product design solutions are as shown below:

The electric light source device is designed into a self-ballasted bulb structure with built-in driving power supply, so that it can access the municipal electricity for use, which facilitates application in ordinary lamp base or lights. In the meanwhile, many UV lamp tubes are designed into an integrated lamp tube. Specifically speaking, many tubes of the lamp tube are provided around the reflection column, many tubes are connected in sequence, the end of the first tube and that of the last tube are provided with the first electrode and the second electrode respectively to form an independent enclosing-type sealed lamp tube. The new lamp tube can emit 360° light around the reflection column and can be started with only one driving power supply device. Compared with UV germicidal lights which adopt many independent lamp tubes and several driving power supply devices, the electric connection process of the present invention can be significantly simplified, and the cost of the lamp tube and the driving power supply can be reduced.

The driving power supply is provided inside the lamp housing, the lamp housing is provided at one end of the lamp tube with an electrode, the top of the lamp housing is provided with a lamp cap which can be used for external installation of the electric light source device; the bottom of the lamp housing is provided with connecting fitting, and many tubes of the lamp tube are fixed onto the connecting fitting to realize installation of the lamp tube.

In addition, there is also a reflection column inside the tubes which are arranged in a circular shape, which can improve the utilization rate of UV light; there is also a net enclosure on the outer side of the lamp tube to protect the lamp tube. Furthermore, the structure of the net enclosure and that of the reflection column are optimized. The net enclosure is designed into a structure with simple support pillars and protective rings. The connecting fitting and supporting fitting are provided with several mounting holes corresponding to the support pillars which are inserted into the corresponding mounting holes in a flexible way, and connecting fitting and supporting fitting are fixed to columns via screws to clamp the net enclosure. Compared with ordinary net enclosures which are directly fixed with screws or nuts, this clamping installation mode of the net enclosure is featured with simple assembly, low requirement for the processing precision of the net enclosure and significant reduction of the cost.

Additionally, the supporting fitting is also provided with the second light outlets corresponding to lamp tubes, which enables the UV light to be emitted out of the product via the second light outlets, so that the light illumination angle of the electric light source device can be increased; the bottom of the supporting fitting is provided with a sensor which is used for turning off the light source when human bodies nearby the UV light are detected to guarantee the use safety. Additionally, the top of the supporting fitting nearby the lamp tube is also provided with a reflective surface used for reflecting UV light emitted onto the supporting fitting for utilization to improve the utilization rate of UV light, and the reflective surface can also prevent UV light from being emitted onto the sensor, so that use of the sensor will not be affected.

Furthermore, the reflection column is of a thin and long hollow structure. The thin structure can reduce dimensions of the cross section of the lamp tube and make the structure of the electric light source device compact. In one example of 85 W UV electric light source, its dimensions can reduce to φ 90×300 MM, and it can serve as self-ballasted bulb.

The shape, dimension, proportion or position relationship of parts of the product in drawings may be real data of examples and they are under protection of this invention.

DETAILED DESCRIPTION OF THE EMBODIMENTS

To make the objective, technical solutions and advantages of the present invention clearer and be understood better, further detailed descriptions of examples of the present invention are made in combination with drawings. Understandably, the specific examples described are just used to explain but not limit the present invention.

Figure 1:
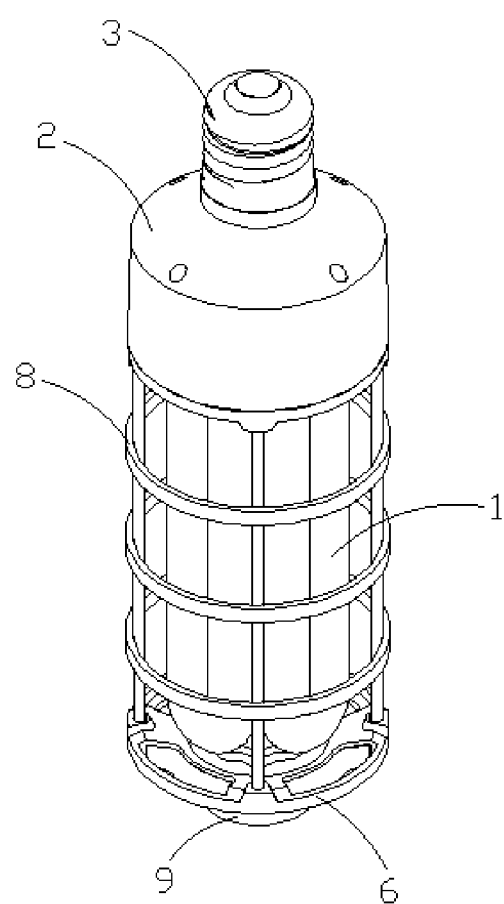
FIG. 1 is a schematic diagram showing the structure of the electric light source device of the present invention.
Figure 2:
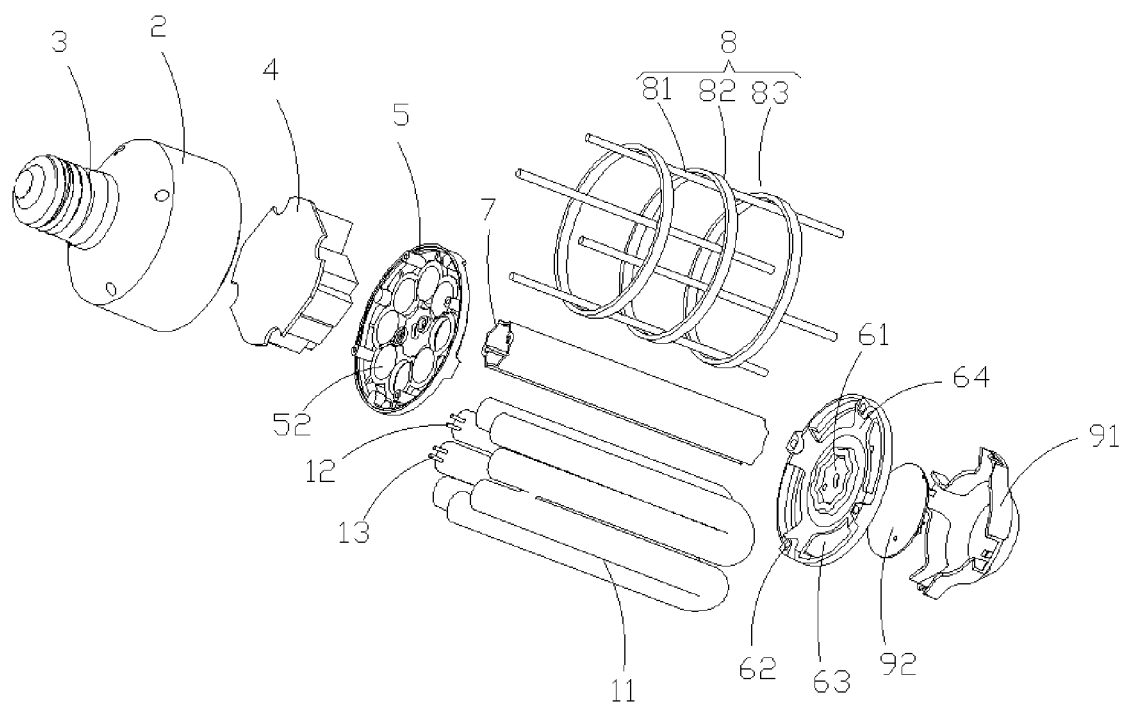
FIG. 2 is a schematic diagram showing the breakdown/explosion structure of the electric light source device of the present invention.
Figure 3:
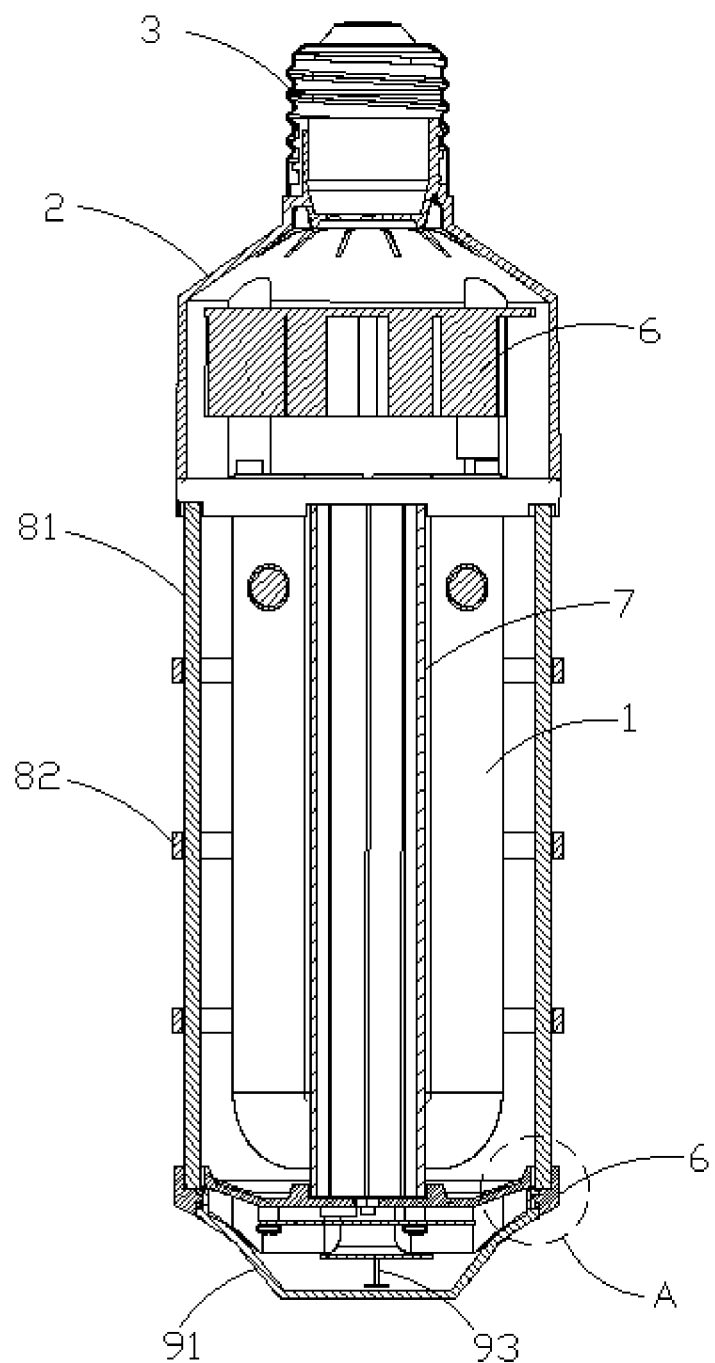
FIG. 3 is a section view of one part of the electric light source device of the present invention.
Figure 4:
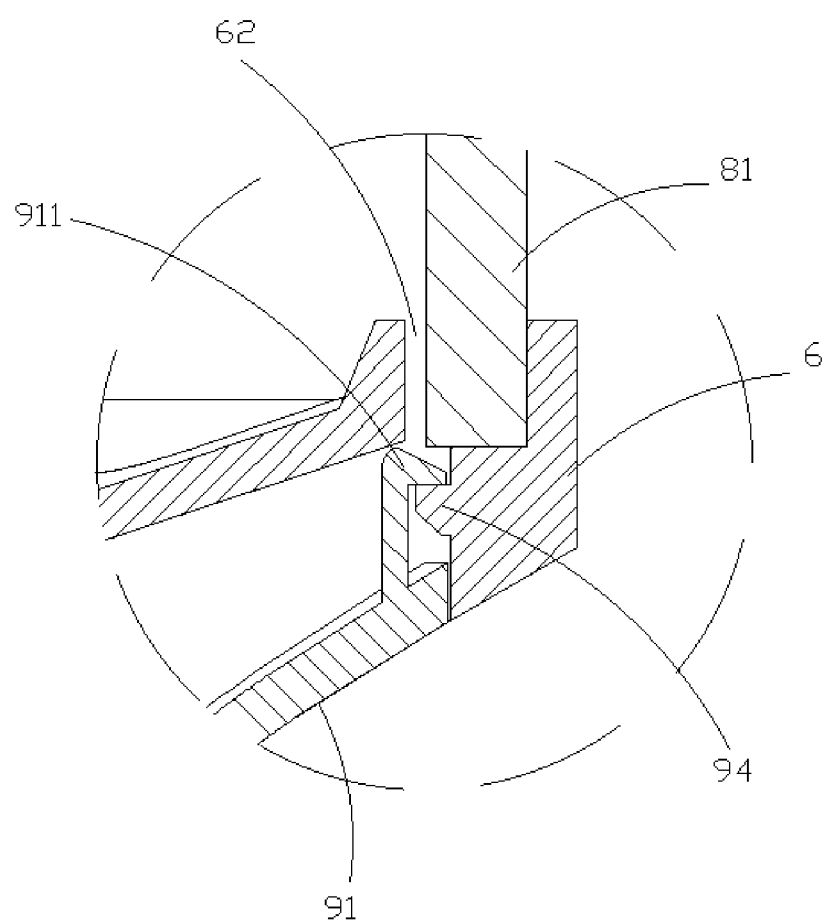
FIG. 4 is an enlarged view of position A in FIG. 3.
Figure 5:
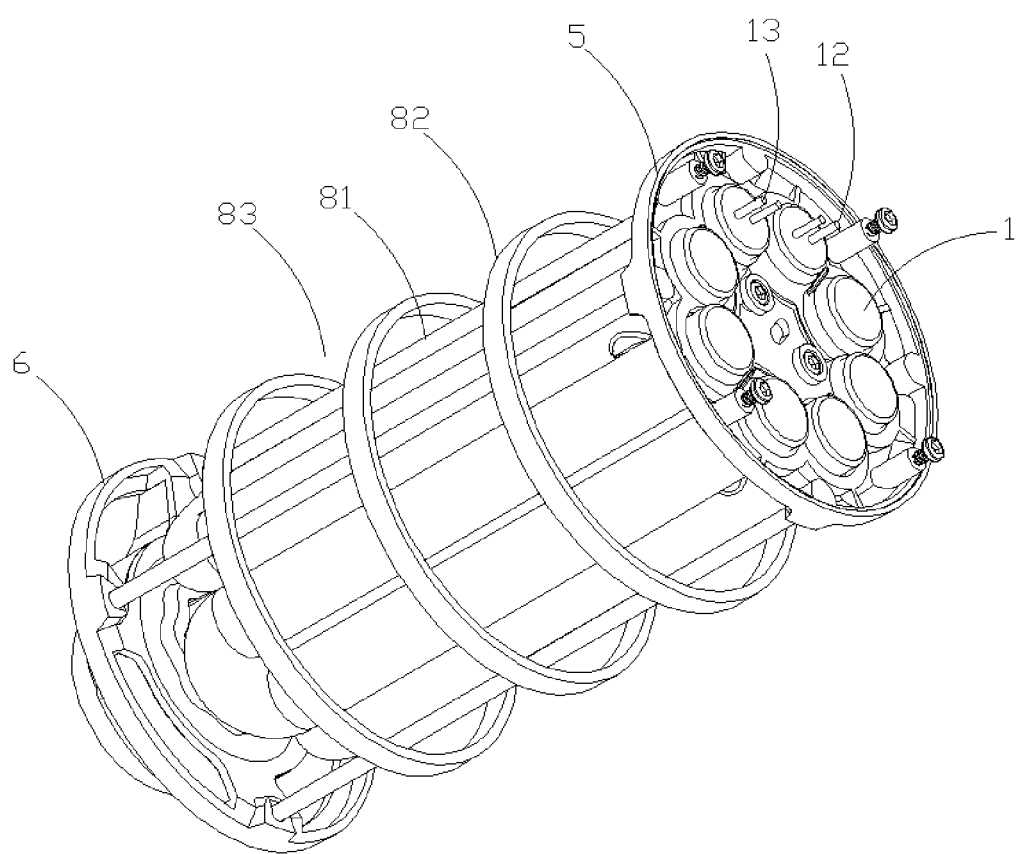
FIG. 5 is a schematic diagram showing installation of the lamp tube.

As shown in FIGS. 1-3, large-power UV sterilization electric light source devices usually need to adopt many UV lamp tubes to improve their power and shorten the UV sterilization time. However, many UV lamp tubes need many driving power supply devices, and each UV lamp tube needs to connect four power supply output ends, which will cause difficult electrical connection process and a high cost of lamp tubes and driving power supply. With many UV lamp tubes and many driving power supply devices, products will have a large volume, it is hard to directly install such products inside ordinary lamp enclosures, the compatibility is poor and it is inconvenient in use. And, the UV lamp tube cannot be protected well, or there is not a structure for protecting the UV lamp tube. Thus, the present invention provides an electric light source device and lamp, wherein the lamp is provided with the electric light source device, the electric light source device comprises a lamp cap 3, a lamp housing 2, a connecting fitting 5, a reflection column 7 and a supporting fitting 6 which are connected in sequence from the top to the bottom and also a lamp tube 1, a net enclosure 8 and the driving power supply 4 provided inside the lamp housing 2 and a lamp tube 1 which is composed of several tubes 11 connected in sequence around the reflection column. The lamp tube 1 can emit UV light for sterilization and disinfection. The top of the first tube is provided with the first electrode 12, and the end of the last tube is provided with the second electrode 13 to form an independent enclosing-type sealed lamp tube 1 which can emit 360° light around the reflection column and can be started with only one driving power supply device 4. Compared with UV germicidal lights which adopt many independent lamp tubes and several driving power supply devices, the electric connection process of the present invention can be significantly simplified, the cost of the lamp tube 1 and the driving power supply 4 can be reduced, and the volume of the electric light source device can be reduced.

Lamp housing 2 is provided at one end of the tubes 11 with an electrode, the top of the lamp housing 2 is provided with a lamp cap 3 which can be used for external installation of the electric light source device, the bottom of the lamp housing 2 is provided with a connecting fitting 5, several tubes 11 of the lamp tube 1 are fixed onto the connecting fitting 5 to realize installation of the lamp tube 1. The driving power supply 4 is provided inside the lamp housing 2 and can access the municipal electricity directly, which facilitates application of the present invention in ordinary lamp base or lights; reflection column 7 can improve the utilization efficiency of the UV light, and the net enclosure 8 is provided on the outer side of the lamp tube 1 to protect the lamp tube 1.

Under understanding of the technicians in this technical field, the driving power supply 4 can be ballast.

As shown in FIGS. 1-11, in one example of the present invention, the electric light source device comprises a lamp tube 1, a lamp housing 2, a lamp cap 3, a driving power supply 4, a connecting fitting 5, a supporting fitting 6, a reflection column 7, a net enclosure 8 and a control module 9. In this example, the arrow "up" means the up direction, the arrow "down" means the down direction, and the up-down direction can also mean the longitudinal direction.

As shown in FIGS. 1-3, the lamp tube 1 comprises several tubes 11 which are connected in sequence around the reflection column 7, the end of the first the tube is provided with the first electrode 12, the end of the last tube is provided with the second electrode 13, the first electrode 12 and the second electrode 13 electrically connect to the driving power supply 4, the electric light source device can be started only with one piece of driving power supply 4, lamp housing 2 is provided at one end of the lamp tube 1 with an electrode, the driving power supply 4 is provided inside the lamp housing 2, the top of the lamp housing 2 is provided with a lamp cap 3, the bottom of lamp housing 2 is provided with a connecting fitting 5, several tubes 11 of the lamp tube 1 are provided on the connecting fitting 5 to realize installation of the lamp tube 1.

Figure 6:
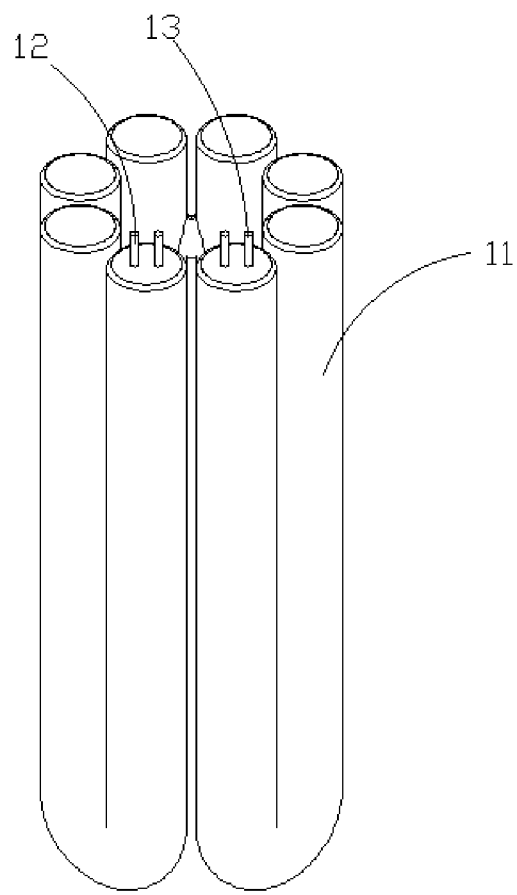
FIG. 6 is a schematic diagram showing the structure of the lamp tube.

As shown in FIG. 6, in one example of the present invention, both ends of the tubes 11 are of an enclosed structure, which forms an enclosing-type sealed lamp tube 1, tubes 11 are of a U-shape structure, the opening of the U-shape structure faces the lamp housing 2, tubes 11 have two upright sections, and there is a certain distance between the connecting point of tubes 11 and the end of tubes 11, which facilitates assembly of tubes 11 with connecting fitting 5.

As shown in FIGS. 2-5 and FIG. 8, the connecting fitting 5 and the supporting fitting 6 are opposite to each other on both sides of the lamp tube 1, the connecting fitting 5 is provided at the bottom of the lamp housing 2, and according to understanding of the technicians in this technical field, the connecting fitting 5 can fixed to the lamp housing 2 via a lamp or screw. The connecting fitting 5 is provided with the first mounting hole 51 and the first fixing holes 52, and the mounting hole positions of the connecting fitting 5 comprise several second fixing holes 53. The first mounting hole 51 is provided in the middle of the connecting fitting 5, the first mounting hole 51 is a blind hole used for installing the reflection column 7; the first fixing holes 52 are provided around the first mounting hole 51, and the first fixing holes 52 are used for installing the tubes 11 of the lamp tube 1.

Preferentially, the quantity of the first fixing holes 52 is the same as that of the tubes 11, one upright section of tubes 11 is corresponding to one first fixing hole 52, after the end of the tubes 11 extends into the first fixing holes 52, tubes 11 can be fixed with glue or is fixed by setting a rubber gasket between the first fixing hole 52 and the tube 11.

Preferentially, several second fixing holes 53 are provided nearby the rim of the connecting fitting 5 and are distributed evenly along the rim of the connecting fitting 5.

Figure 10:
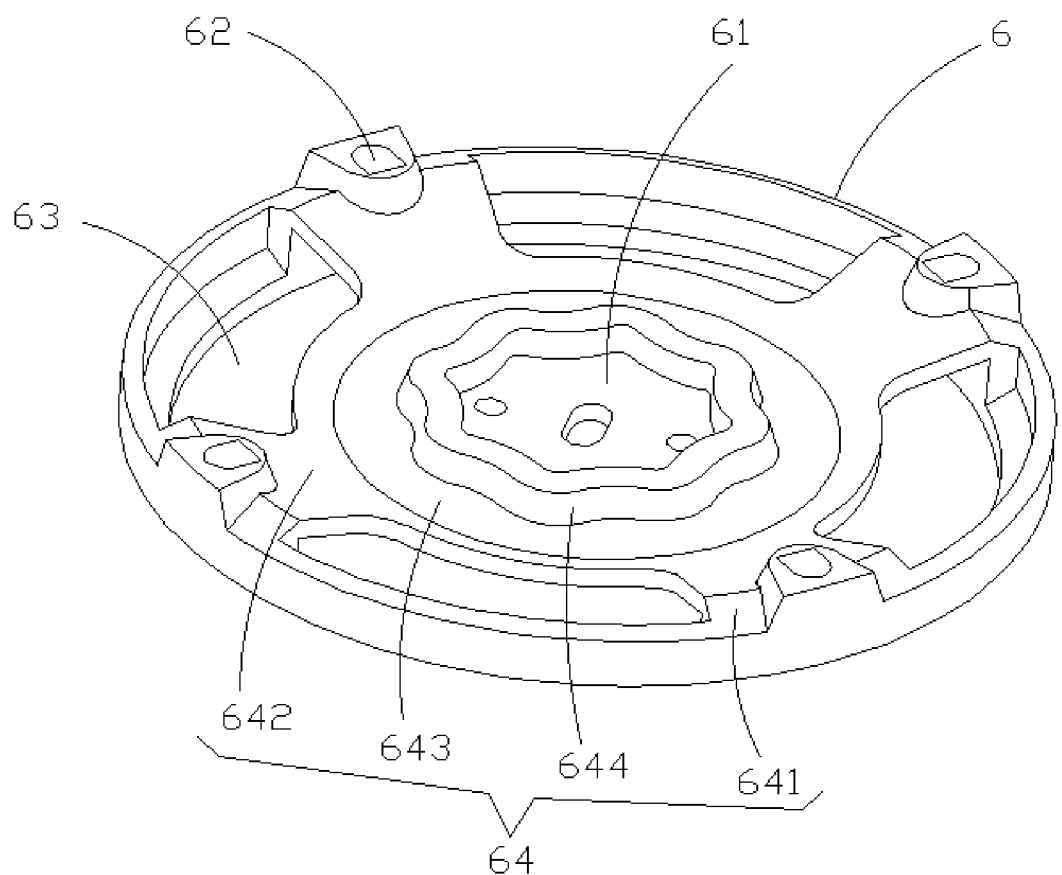
FIG. 10 is a schematic diagram showing the structure of the supporting fitting.
Figure 11:
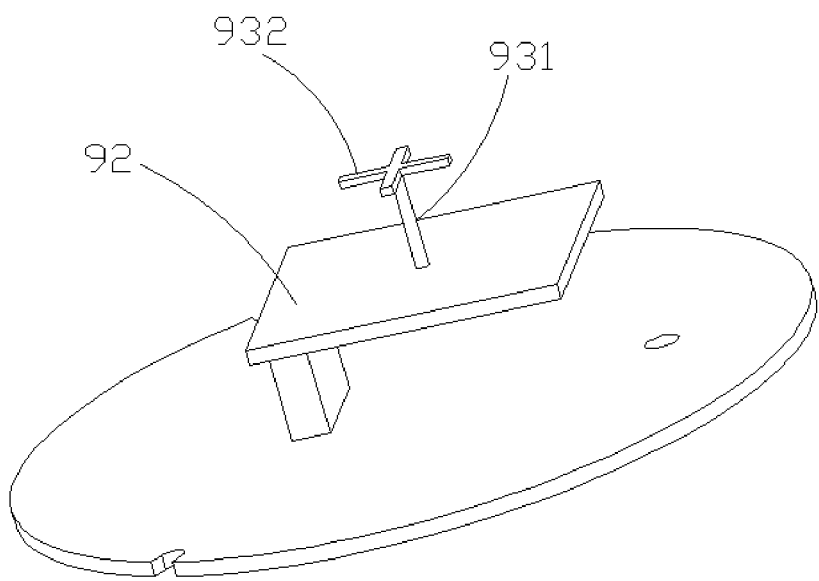
FIG. 11 is a schematic diagram showing the installation of the stereoscopic antenna.

As shown in FIG. 10, the supporting fitting 6 is provided with the second mounting hole 61 and the mounting position, the second mounting hole 61 is provided in the middle of the top of the supporting fitting 6, the second mounting hole 61 is a blind hole, and the second mounting hole 61 is used for installing the reflection column 7; the mounting hole positions of the supporting fitting 6 comprise several third fixing holes 62. Several third fixing holes 62 are provided nearby the rim of the supporting fitting 6 and are arranged evenly along the rim of the supporting fitting 6, the quantity of the second fixing holes 53 is the same as that of the third fixing holes 62, and they are provided correspondingly in the longitudinally direction, which facilitates installation and fixing of the net enclosure 8. In one example of the present invention, the connecting fitting 5 and the supporting fitting 6 are in the disc shape, and there are four second fixing holes 53 and four third fixing holes 62. The supporting fitting 6 corresponding to the bottom of the lamp tube 1 is provided with the second light outlets 63, the UV light emitted by the lamp tube 1 can go out of the product via the second light outlets 63, the third fixing holes 62 are provided between two adjacent second light outlets 63, which enables the support pillars 81 to reduce shielding of UV light.

The top of the supporting fitting 6 is provided with a reflective surface 64, and partial UV light emitted by the lamp tube 1 is reflected by the reflective surface to the first light outlets 83 or to the reflection column 7. The reflective surface 64 comprises the first inclined plane 641, the cambered surface 642, the plane 643 and the second inclined plane 644, and the plane 643 is vertical to the reflection column 7; a circular boss is formed on the periphery of the second mounting hole 61, the outer side of the circular boss is inclined to form the second inclined plane 644, and the reflective surface can realize multi-angle reflection of light rays to improve the light illumination efficiency of the electric light source device. The cambered surface 642, the plane 643 and the second inclined plane 644 compose a concave upward reflective surface, i.e. a concave surface facing the connecting fitting 5; in other examples, the reflective surface 64 can also be a concave reflective surface in other shapes. Preferentially, the reflection column 7 is made of aluminum alloy.

Figure 7:
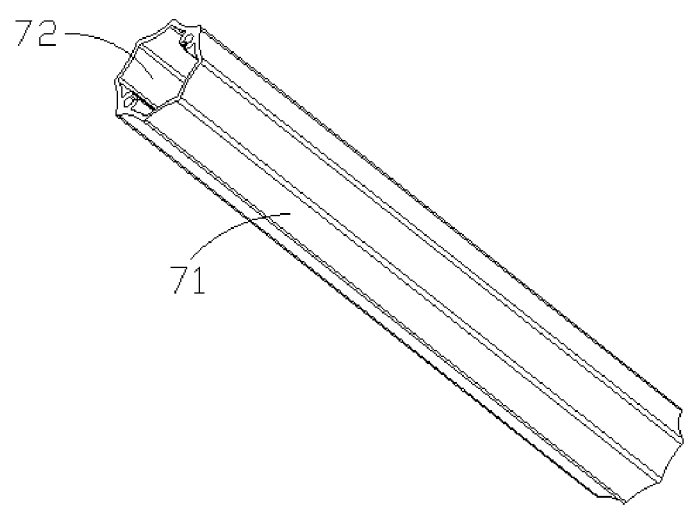
FIG. 7 is a schematic diagram showing the structure of the reflection column.
Figure 8:
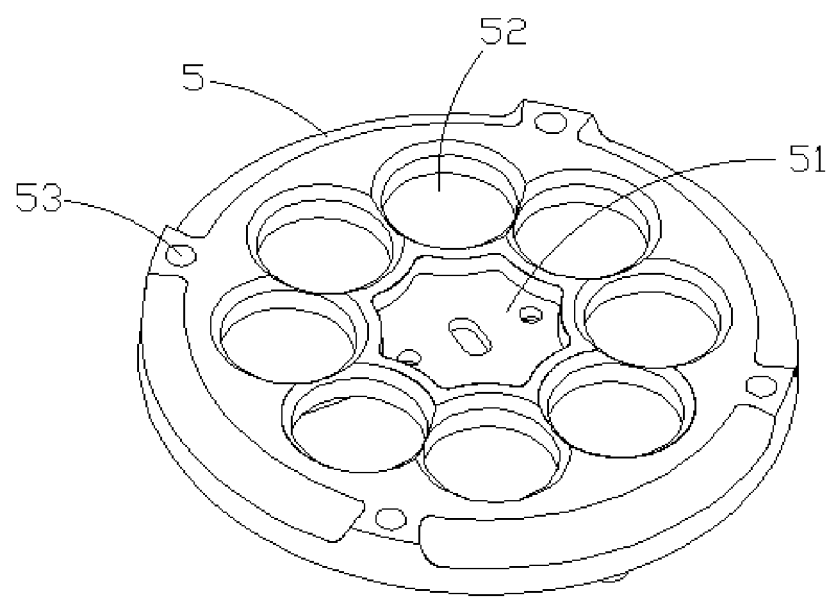
FIG. 8 is a schematic diagram showing the structure of the connecting fitting.
Figure 9:
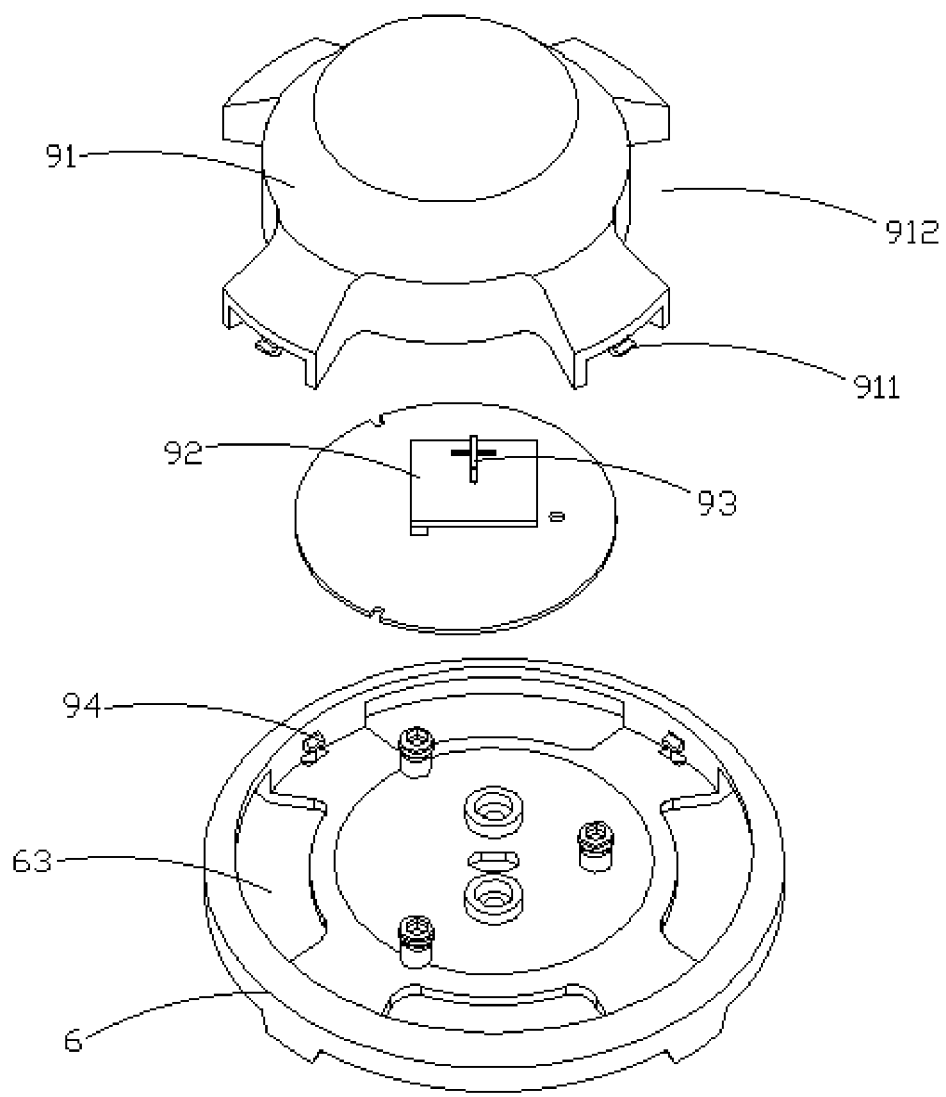
FIG. 9 is a schematic diagram showing the breakdown of the supporting fitting and the control module.

As shown in FIG. 3 and FIG. 7, the tubes 11 of the lamp tube 1 are arranged around the reflection column 7 which has two opposite ends (the first end and the second end), the first end of the reflection column 7 is provided inside the first mounting hole 51, the second end of the reflection column 7 is provided inside the second mounting hole 61, the first end and the second end of the reflection column 7 and the second mounting hole 61 are provided with screw holes which enable the reflection column 7 to be fastened with the connecting fitting 5 and the supporting fitting 6 respectively. To improve the utilization efficiency of the light source, the reflection column 7 corresponding to the upright section of tubes 11 is provided with a concave surface 71 which reflects light rays emitted onto the reflection column 7; the reflection column 7 is also provided with a cord hole 72 which runs through the axial direction and can be used for laying lead wire.

As shown in FIGS. 2-3, the net enclosure 8 is provided on the outer side of the lamp tube 1, the net enclosure 8 possesses support pillars 81 and protective rings 82 which form the first light outlets 83, and the UV light emitted by the lamp tube 1 can go out of the product via the first light outlets 83; the concave surface 71 reflects UV light emitted onto the reflection column 7 to the first light outlets 83. There are several support pillars 81 and several protective rings 82. Several protective rings 82 are provided at intervals longitudinally, and the support pillars 81 are vertical to the plane where each protective ring 82 is located to form several first light outlets 83. One end of the support pillars 81 is provided in the second fixing holes 53 on the connecting fitting 5, and the other end is provided in the third fixing holes 62 on the supporting fitting 6. In the present invention, the second fixing holes 53 and the third fixing holes 62 are only used for limiting the position of the support pillars 81, after the reflection column 7 connects to the connecting fitting 5 and the supporting fitting 6 respectively in a fixed way, the connecting fitting 5 and the supporting fitting 6 can clamp the support pillars 81, preventing the net enclosure 8 from directly connecting to connecting fitting 5 and supporting fitting 6 in a fixed way. Compared with ordinary net enclosures which are directly fixed with screws, installation in the clamping way enables simple disassembly and installation of the net enclosure 8, reduces the assembly difficulty of the net enclosure 8, does not have high requirements for the processing precision of the net enclosure 8, significantly reduces the cost of the net enclosure 8.

As shown in FIGS. 2-4 and FIGS. 9-11, the control module 9 is installed at the bottom of the supporting fitting 6, the control module 9 comprises the enclosure 91 and the sensor 92, and the sensor 92 is used for turning off the lamp tube 1 when human bodies approach the electric light source device. The sensor 92 can connect the supporting fitting 6 with screws, and the enclosure 91 covers the outside of the sensor 92 to protect the sensor 92. The sensor may be a microwave sensor or an infrared sensor.

Preferentially, in one example of the present invention, the sensor 92 is a microwave sensor whose top is provided with a stereoscopic antenna 93, and the downward side of the sensor 92 is the top of the sensor 92. The stereoscopic antenna 93 comprises the vertical antenna column 931 and the horizontal antenna 932, the upper end of the vertical antenna column 931 connects to the main body of the sensor 92, and the lower end of the vertical antenna column 931 connects to the horizontal antenna 932. The signal receiving antenna of the microwave sensor of existing lights is usually provided on the circuit board on their top, the copper foil of the circuit board serves as the antenna, the antenna is distributed on the surface of the circuit board, so the sensing sensitivity is relatively poor; While the present invention adopts the design of the stereoscopic antenna 93 provided on the top of the sensor 92, which can improve the signal receiving scope and receiving capability of the sensor 92 and thus improve the use safety of the electric light source device, improve the sensitivity of the sensing signal and save the cost of the sensor 92 by avoiding use of several sensors 92.

In one example of the present invention, to avoid that the enclosure 91 shields the UV light emitted from the second light outlets 63, the enclosure 91 is provided with gaps 912 corresponding to the second light outlets 63, partial UV light emitted by the lamp tube 1 can go out of the bottom of the electric light source device via the second light outlets 63 and the gaps 912.

The enclosure 91 is snap-fitted with the supporting fitting 6, the enclosure 91 is provided with the first snap joint 911 whose head is provided outward. The bottom of the supporting fitting 6 is provided with a bottom walls and side walls 65, the side walls 65 are provided with second snap joints 94, the head of the second snap joints 94 is provided inward, and the second snap joints 94 are at the bottom of the third fixing holes 62, which simplifies the module structure of the supporting fitting 6 and the module cost; and it is also convenient for disassembly of the enclosure 91 from the bottom of the supporting fitting 6 and repair of the product.

The examples of the present invention also provide a lamp provided on the above electric light source device.

On the above structure and principle, the lamp cap 3 is not only limited to ordinary screw base or snap joint base (e.g. E27 and B22), the lamp cap 3 can also be deemed as a mounting base with which the lamp is directly installed in illuminating or sterilization places, that is, the electric light source device is used as a light.

Optionally, the illumination mode of the lamp tube emits 350-750 nm visible light instead of UV light, so that the electric light source device is suitable for illuminating places. In examples of the present invention, the lamp tube may be provided as a UV lamp tube or a visible light tube, and the corresponding electric light source devices are of good practical values.

The above description only presents the preferred examples of the invention, and it is not for this reason that the patent scope of the invention is limited. Any equivalent structural transformation made by using the description of the invention and the drawings, or direct/indirect application in other related technical fields under the inventive concept of the invention, is included in the patent protection scope of the invention.

What is claimed is:

1. An electric light source device, comprising:
    a lamp cap, a lamp housing, a connecting fitting, a reflection column and a supporting fitting which are connected in sequence from a top to a bottom of the electric light source device,
    wherein the electric light source device further comprises a lamp tube, a net enclosure, and a driving power supply provided inside the lamp housing;
    wherein the lamp tube is provided at a bottom of the connecting fitting and comprises several tubes which are connected in sequence and are provided around the reflection column,
    wherein an end of the first the tube and an end of the last tube are provided with a first electrode and a second electrode respectively,
    wherein the first electrode and the second electrode electrically connect to the driving power supply, respectively;
    wherein the net enclosure is provided on an outer side of the lamp tube and connects to the connecting fitting or the lamp housing,
    wherein the net enclosure is provided with several first light outlets through which UV light may pass,
    wherein the supporting fitting is provided with several second light outlets through which UV light may pass and which are provided at ends of the tubes,
    wherein a top of the supporting fitting is provided with a concave reflective surface facing the connecting fitting for reflecting at least some of the UV light emitted by the lamp tube through the first light outlets or to the reflection column,
    wherein the net enclosure comprises several support pillars and at least one protective ring which delimit at least one of the first light outlets,
    wherein the connecting fitting is provided with several second fixing holes corresponding to the support pillars, the supporting fitting is provided with several third fixing holes corresponding to the support pillars, and the third fixing holes are provided between two adjacent second light outlets,
    wherein both ends of the support pillars are respectively provided in the second fixing holes and the third fixing holes; and the connecting fitting and the supporting fitting are fixed on the reflection column and clamp the net enclosure therebetween,
    wherein a bottom of the supporting fitting is provided with a control module which comprises:
        a sensor used for turning off the lamp tube when human bodies approach the electric light source device; and
        an enclosure, provided on an outer side of the sensor,
    wherein the enclosure is provided with a first snap joint and gaps corresponding to the second light outlets,
    wherein the bottom of the supporting fitting is provided with a second snap joint corresponding to the third fixing holes,
    wherein the second snap joint is arranged opposite to the third fixing holes, and
    wherein the first snap joint is snap-fitted with the second snap joint.

2. The electric light source device as claimed in claim 1, wherein the reflection column is formed as a thin and long hollow structure,
    wherein a periphery of the reflection column is provided with a concave surface corresponding to an upright portion of the tubes and the concave surface can reflect UV light,
    wherein the reflection column is provided with a cord hole which runs through an axis of the reflection column for laying wire; and/or
    wherein the connecting fitting is provided with a first mounting hole, the supporting fitting is provided with a second mounting hole, the reflection column comprises a first end and a second end which are opposite to each other, the first end is provided inside the first mounting hole, and the second end is provided inside the second mounting hole; and/or
    wherein the reflection column is made of aluminum alloy; and/or
    wherein the bottom of the supporting fitting is provided with a control module used for turning off the lamp tube when there are human bodies nearby.

3. The electric light source device as claimed in claim 1, wherein the protective rings are provided at intervals longitudinally, and the support pillars are vertical to the plane of each the protective ring.

4. The electric light source device as claimed in claim 1, wherein the bottom of the supporting fitting is provided with a control module; and/or
   wherein the sensor is a microwave sensor, a top of the sensor is provided with a stereoscopic antenna which is used for receiving microwave signals, and the stereoscopic antenna comprises a vertical antenna column and a horizontal antenna.

5. The electric light source device as claimed in claim 1, wherein a back of the supporting fitting possesses a side wall, and the second snap joint is provided on the side wall with a snap joint head facing inward.

6. The electric light source device as claimed in claim 1, wherein the lamp tube emits 350-750 nm visible light instead of UV light, and the lamp tube is used for lighting.

7. A lamp comprising the electric light source device according to claim 1.

\* \* \* \* \*